(12) United States Patent
Stickney et al.

(10) Patent No.: US 7,985,777 B2
(45) Date of Patent: Jul. 26, 2011

(54) SYSTEMS AND METHODS FOR REACTIVE DISTILLATION WITH RECIRCULATION OF LIGHT COMPONENTS

(76) Inventors: Michael J. Stickney, Nassau Bay, TX (US); Edward M. Jones, Jr., Friendswood, TX (US)

( * ) Notice: Subject to any disclaimer, the term of this patent is extended or adjusted under 35 U.S.C. 154(b) by 258 days.

(21) Appl. No.: 12/261,869

(22) Filed: Oct. 30, 2008

(65) Prior Publication Data
US 2010/0113625 A1    May 6, 2010

(51) Int. Cl.
*C07C 27/00* (2006.01)
(52) U.S. Cl. ........................ 518/705; 518/700
(58) Field of Classification Search .................. 518/700, 518/705
See application file for complete search history.

(56) References Cited

FOREIGN PATENT DOCUMENTS
WO    WO 01/36066 A2  *  5/2001

OTHER PUBLICATIONS

Malone et al., Green chemical engineering aspects of reactive distillation, (Environmental science and Technology (2003), 37 (23), 5325-55329).*

* cited by examiner

*Primary Examiner* — Jafar Parsa
(74) *Attorney, Agent, or Firm* — Edmonds & Nolte, P.C.

(57) ABSTRACT

Systems and methods for producing gas-to-liquids products using reactive distillation are provided. The method for producing gas-to-liquids products can include reacting a feedstock in a column having a distillation zone and a reaction zone to provide a bottoms stream and an overhead stream. A first portion of the overhead stream can be recycled to the column at the top of the reaction zone and second portion of the overhead stream can be recycled to the column at the bottom of the reaction zone.

17 Claims, 6 Drawing Sheets

SYSTEMS AND METHODS FOR REACTIVE DISTILLATION WITH RECIRCULATION OF LIGHT COMPONENTS

FEDERALLY SPONSORED RESEARCH OR DEVELOPMENT

This invention was made, in part, with support awarded by the United States Department of Energy under Grant No.: DE-FG02-0404ER83999. The United States government may have certain rights in this invention.

BACKGROUND OF THE INVENTION

1. Field of the Invention

Embodiments of the present invention generally relate to systems and methods for producing gas-to-liquids products. More particularly, embodiments relate to systems and methods for producing gas-to-liquids products using reactive distillation.

2. Description of the Related Art

Hydrocarbon gases can be reacted to provide liquid hydrocarbon materials, such as diesel and/or gasoline components, and other useful products. Such reactions are typically catalyzed using Fixed bed or slurry reactors. A disadvantage, however, of using a fixed bed or slurry reactor configuration is that a wide variety of molecular-weight compounds are present within the reactor at one time.

In a Fischer-Tropsch reaction, for example, the molecular chains continue to grow as long as the reactants and products remain in contact with the catalyst. There is little control over chain growth in a fixed bed or slurry reactor, which causes undesirable high molecular-weight products, such as heavy hydrocarbon waxes to be produced. These waxy products are prone to poisoning and/or fouling the reaction catalyst more quickly than lower molecular-weight products. Furthermore, if the desired products are gasoline and diesel, for example, such heavy hydrocarbons are beyond the desired molecular-weight range.

Additional steps to purify the intended products are usually required to mitigate such disadvantages. Conventional methods for removing the unwanted heavy hydrocarbons, however, require additional hydrocracking equipment to crack the heavy hydrocarbons to provide products within the desired molecular-weight range. This additional equipment is expensive to construct, install, maintain, and operate. Such additional equipment is also energy intensive and adds to the footprint of the overall process.

There is a need, therefore, for improved systems and methods for reacting gases derived from hydrocarbons to provide products having a reduced amount of unwanted heavy hydrocarbons.

SUMMARY

Systems and methods for producing gas-to-liquids products using reactive distillation are provided. In at least one specific embodiment, the method for producing gas-to-liquids products can include reacting a feedstock in a column having a distillation zone and a reaction zone to provide a bottoms stream and an overhead stream. In one or more embodiments, a first portion of the overhead stream can be recycled to the column at the top of the reaction zone. In one or mole embodiments, a second portion of the overhead stream can be recycled to the column at the bottom of the reaction zone.

In at least one other specific embodiment, the method for producing gas-to-liquids products can include introducing one or more reactants to a reactive distillation column containing a reaction zone and a distillation zone therein. In one or more embodiments, the one or more reactants can be reacted in the presence of a catalyst in the reaction zone to provide an overhead and an intermediate product. In one or more embodiments, the intermediate product can be selectively separated into two or more distillate fractions. In one or more embodiments, the overhead can be separated into at least a first position and a second portion, and the first and second portions can be recycled to different locations within the reaction zone.

In at least one other specific embodiment, the method for producing gas-to-liquids products can include introducing one or more reactants to a reactive distillation column containing a reaction zone and a distillation zone therein. In one or more embodiments, the one or more reactants can be reacted in the presence of a catalyst in the reaction zone to provide an overhead and an intermediate product. In one or more embodiments, the overhead can be a gas. In one or more embodiments, a portion of the overhead can be cooled to provide a two-phase mixture. In one or more embodiments, the liquid can be separated from the two-phase mixture to provide a first liquid recycle and a first gas recycle. In one or more embodiments, at least a portion of the first liquid recycle can be recycled to the reaction zone and at least a portion of the first gas recycle can be recycled to the reaction zone. In one or more embodiments, the first liquid recycle and the first gas recycle can be introduced to different locations within the reaction zone.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Figure 1:
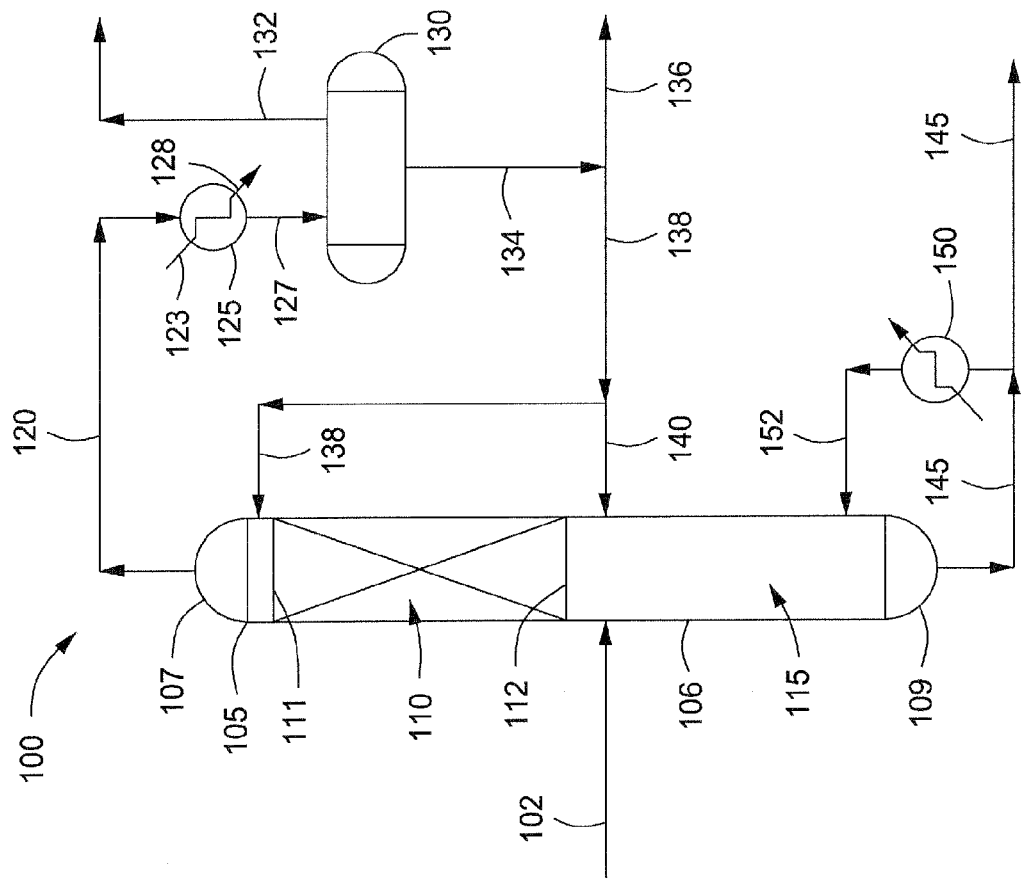
FIG. 1 depicts an illustrative reactive distillation system according to one or more embodiments described.

FIG. 1 depicts an illustrative reactive distillation system 100 according to one or more embodiments. In one or more embodiments, the reactive distillation system 100 can include, but is not limited to, one or more reactive distillation columns 105, one or more heat exchangers 125, 150, and one or more gas/liquid separation vessels 130. The separation vessels 130 can be horizontal or vertical, and can be any tank, drum, or other container capable of separating at least a portion of any gas in a liquid/gas mixture.

In one or more embodiments, the distillation column 105 can include a shell or housing 106 that contains two or more zones or sections therein. Two zones are depicted in FIG. 1, namely a first ("reaction") zone 110 having one or more catalysts disposed therein and a second ("distillation") zone 115. In one or more embodiments, the reaction zone 110 can be disposed toward a first end 107 of the distillation column 105 and the distillation zone 115 can be disposed toward a second end 109 of the distillation column 105.

A reactant or feedstock via line 102 can be introduced to the distillation column 105 where the reactant can react with the one or more catalysts within the reaction zone 110 to provide an overhead via line 120. The reactions between the reactant and the one or more catalysts within the reaction zone 110 can include, but are not limited to chain growth reactions. Illustrative chain growth reactions can include oligomerizations and polymerizations, such as Fischer-Tropsch reactions. Another suitable chain growth reaction can include the formation of polyisobutylenes and other long chain alpha olefins, which can be used in the pharmaceutical and food industries, for example.

For simplicity and ease of description, the reaction type discussed herein is in the context of a chain growth reaction, namely a Fischer-Tropsch reaction. However, it is understood that other suitable types of reactions are also contemplated and within the scope of this disclosure. Those skilled in the art will also recognize that any suitable catalyst, number of reaction zones 110, number of distillation zones 115, and reactants introduced via line 102 can be used.

At least a portion of the overhead via line 120 can be introduced to the one or more heat exchangers 125. The one or more heat exchangers 125 can indirectly transfer heat from the overhead introduced via line 120 to a heat transfer medium introduced via line 123. Cooling the overhead can condense at least a portion of any gas in the overhead to provide a cooled product via line 127 of which at least a portion includes a condensed or liquid product. A warmed heat transfer medium via line 120 can be recovered from the one or more heat exchangers 125.

The cooled product via line 127 can be introduced to the separation vessel 130 to separate at least a portion of any uncondensed gas via line 132 from the cooled product in line 127. A liquid product can be recovered from the separation vessel 130 via line 134. In one or more embodiments, at least a portion of the liquid product in line 134 can be recovered as a product via line 136, and/or at least a portion of the liquid product in line 134 can be recycled to the reaction zone 110 via line 138 and/or line 140.

In one or more embodiments, a first portion of the condensed product ("primary recycle") via line 138 can be introduced to a first end 111 of the reaction zone 110 disposed toward the first end 107 of the distillation column 105, or to any other location within the reaction zone 110. In one or more embodiments, a second portion of the condensed product ("secondary recycle") via line 140 can be introduced to a second end 112 of the reaction zone 110 disposed toward the distillation zone 115, or to any other location within reaction zone 110. In one or more embodiments, the second portion via line 140 can be introduced to the distillation column 105 between the distillation zone 115 and the second end 112 of the reaction zone 110, or directly to the reaction zone 110. In one or more embodiments, the second portion via line 140 can be introduced to the distillation zone 115.

In one or more embodiments, the lighter products and/or components can flow toward the first end 107 of the distillation column 105 while heavier products and/or components can flow toward the second end 109 of the distillation column 105. The lighter components can include unreacted reactant, light/low boiling reaction products, and other materials. The lighter components can be removed from the column 105 via line 120. Heavier components, including higher-boiling reaction products and other heavy/high-boiling materials, can flow toward the second end 109 of the distillation column 105 via the distillation zone 115. Intermediate-boiling components can be stripped from the heavier components within the distillation zone 115. The lighter stripped components can flow to the reaction zone 110 for repeated contact with the catalyst disposed therein.

As used herein, the terms "light products," "light components," "light molecules," "heavy products," "heavy components," and "heavy molecules" denote "low-boiling" and "high-boiling," products, components, and molecules respectively. Unless otherwise mentioned, "light" and "heavy" refer to respective boiling points and do not necessarily denote actual molecular-weight comparisons.

In one or more embodiments, the temperature within the reaction zone 110 can be controlled or adjusted by controlling the pressure within the reaction zone 110. In one or more embodiments, the pressure within the reaction zone 110 can be controlled or adjusted by controlling the temperature and/or composition of the recycled first portion via line 138, the recycled second portion via line 140, the reactant introduced via line 102, or any combination thereof.

Recycling at least a portion of the overhead via line 138 and/or line 140 can reduce the temperature profile within the reaction zone 110, which can extend from the first end 111 to the second end 112 of the reaction zone 110. Reducing the temperature profile within the reaction zone 110 can provide a reaction zone 110 having an isothermal or near isothermal temperature profile. In fact, recycling at least a portion of the overhead in line 120 via line 138 and/or line 140 can result in an isothermal or near isothermal temperature gradient within the reaction zone 110.

In one or more embodiments, the composition of the first portion via line 138 and the second portion via line 140 can be controlled by adjusting the temperature of the cooled overhead in line 127. An increased concentration of light molecules from the overhead in line 120 to the first portion via line 138 and/or the second portion in line 140 can be provided by increasing the heat transferred from the overhead within the heat exchanger 125 to the heat transfer medium introduced via line 123. A decreased concentration of light molecules from the overhead in line 120 to the first portion via line 138 and/or the second portion in line 140 can be provided by decreasing the heat transferred from the overhead within the heat exchanger 125 to the heat transfer medium introduced via line 123.

By adjusting the temperature of the first portion via line 138 and the second portion via line 140, the compounds the reaction zone 110 can be changed, thereby allowing control over the chain length of the end product(s) or bottoms via line 145 provided by the reaction. Thus, the same distillation reaction system 100 can be used to make different products by running the reactive distillation system 100 at different temperatures and/or pressures. In one or more embodiments, the reactive distillation system 100 can include a control system for monitoring and controlling the temperature and/or pressure within the system. Any control system known in the art can be used. The control system can automatically adjust the temperature and/or pressure of the reaction zone 110 and/or distillation zone 115 by controlling the temperature of the one or more heat exchangers 125 and/or 150.

In one or more embodiments, a ratio of the first portion via line 138 to the second portion via line 140 recycled to the reaction zone 110 can be constant or can vary. In one or more embodiments, the ratio of the first portion via line 138 to the second portion via line 140 recycled to the reaction zone 110 can be systematically varied, randomly varied, varied in response to one or more reaction zone 110 properties, or any combination thereof. Such reaction zone 110 properties can include, but are not limited to, temperature, chemical composition of the product in line 120, pressure, or combinations thereof.

In one or more embodiments, a ratio of the volumetric flow rates of the first portion via line 138 to the second portion via line 140 recycled to the reaction zone 110 can range from a low of about 1:20 to a high of about 20:1, from a low of about 1:15 to a high of about 15:1, or from a low of about 1:10 to a high of about 10:1. In one or more embodiments, the ratio of the first portion via line 138 to the second portion via line 140 recycled to the reaction zone 110 can be about 1:1, about 1:2, about 1:3, about 1:4, about 1:5, about 1:6, about 1:7, about 1:8, or about 1:9. In one or more embodiments, the ratio of the first portion via line 138 to the second portion via line 140 recycled to the reaction zone 110 can be about 2:1, about 3:1, about 4:1, about 5:1, about 6:1, about 7:1, about 8:1, or about 9:1.

In one or more embodiments, the overhead in line 120 can be a gas, a liquid, or a multi-phase mixture. The overhead in line 120 can contain about 50% mol gas, about 60% mol gas, about 70% mol gas, about 80% mol gas, about 90% mol gas, about 95% mol gas, about 98% mol gas, about 99% mol gas, or more. In one or more embodiments, the bottoms in line 145 can be a gas, a liquid, or a multi-phase mixture. The bottoms in line 145 can contain about 50% mol liquid, about 60% mol liquid, about 70% mol liquid, about 80% mol liquid, about 90% mol liquid, about 95% mol liquid, about 98% mol liquid, about 99% mol liquid, or more.

In one or more embodiments, the overhead in line 120, the bottoms in line 145, or both can be multi-component fluids. For example, the overhead in line 120 and/or the bottoms in line 145 can include two or more compounds. In one or more embodiments, an illustrative product scheme for one particular mode of operation of the reactive distillation system 100 carrying out a Fischer-Tropsch reaction, under steady state operating conditions can include introducing a reactant via line 102 that contains hydrogen ("$H_2$") and carbon monoxide ("CO") to the reaction zone 110. The overhead via line 120 can include $C_1$ to $C_{11}$ hydrocarbons and the bottoms via line 145 can include $C_{12}$ to $C_{16}$ hydrocarbons. The liquid product recovered via line 134 can include $C_6$ to $C_{11}$ hydrocarbons, and the uncondensed gases via line 132 can include $C_1$ to $C_5$ hydrocarbons. In another embodiment the liquid product recovered via line 134 can include $C_2$ to $C_{11}$ hydrocarbons and the uncondensed gases via line 132 can include $C_1$ hydrocarbons. The particular composition of the liquid product in line 134 can be controlled or otherwise adjusted via the heat exchanger 125. Thus, it can be seen that multiple product streams can be produced, as desired.

Although not shown, additional products can be recovered from the distillation column 105. For example, one or more products, e.g. a third product or intermediate product, can be recovered from the reaction zone 110, the distillation zone 115, a position between the reaction zone 110 and the distillation zone 115, or a combination thereof. The intermediate product can be a gaseous phase product, a liquid phase product, or a multi-phase mixture.

In one or more embodiments, the rate of introduction to the reaction zone 110 of the first portion via line 138 and/or the second portion via line 140 can be independently varied, remain constant, systematically varied, varied in response to one or more reaction zone 110 properties, or any combination thereof. Such reaction zone 110 properties can include, but are not limited to, temperature, chemical composition of the product in line 120, pressure, or combinations thereof. In at least one specific embodiment, the first portion via line 138 can be introduced at a constant rate and the second portion via line 140 can be introduced at a varying rate. In another embodiment, the second portion via line 140 can be introduced at a constant rate and the first portion via line 138 can be introduced at a varying rate.

In one or more embodiments, at least a portion of the bottoms in line 145 can be heated or cooled via heat exchanger 150, and returned or recycled to the distillation zone 115 via line 152. Recycling at least a portion of the bottoms recovered via line 145, either heated or cooled, to the distillation zone 115 can maintain, adjust, or otherwise control the temperature within the distillation zone 115.

In one or more embodiments, the reactant in line 102 can be a gas, liquid, or a multi-phase mixture. In one or more embodiments, the reactant in line 102 can be a multi-component reactant. Illustrative components of the reactant in line 102 can include, but are not limited to, $H_2$, CO, carbon dioxide ("$CO_2$"), nitrogen, oxygen, methane, ethane, ethylene, propane, propylene, other $C_1$-$C_{20}$ hydrocarbons, or any combination thereof. The particular components of the reactant in line 102 and ratios of those particular components can be chosen based upon the particular type of reaction, operating conditions, desired products, or any combination thereof.

In at least one specific embodiment, the reactant in line 102 can be or include syngas. The syngas can be provided from any number of suitable processes. For example, syngas can be provided from a reforming process that converts hydrocarbon gases, such as natural gas, to hydrogen and carbon monoxide. Additional details for an illustrative process for providing syngas can be as discussed and described in commonly assigned U.S. Pat. No. 7,033,569, which is incorporated by reference herein. Other suitable processes for producing syngas can also be used. Illustrative syngas processes can include, but are not limited to steam methane reformers, auto-thermal reformers, catalytic partial oxidation reformers, partial oxidation reformers, hydrocarbon reforming units and combinations thereof.

Although not shown, the reactant in line 102 can be introduced to the distillation column 105 via a single line or via multiple lines. In one or more embodiments, a reactant that includes $H_2$ and CO can be introduced as separate components via two lines. In another embodiment, a three component reactant that includes, for example $H_2$, CO, and $CO_2$ can be introduced as separate components via three lines. In another embodiment a three component reactant that includes, for example $H_2$, CO, and $CO_2$ can be introduced via two lines, for example a mixture of $H_2$ and CO via one line and $CO_2$ via a second line.

In one or more embodiments, suitable Fischer-Tropsch products via line 120 and/or line 145 can be a mixture of hydrocarbons having a varying range of molecular weights. In one or more embodiments, the products via line 120 and/or line 145 can include $C_1$ to about $C_{40}$ hydrocarbons. For example, the Fischer-Tropsch products via line 120 and/or line 145 can include, but are not limited to, light gaseous hydrocarbons ($C_1$-$C_4$), naphtha ($C_5$-$C_{10}$), diesel ($C_{11}$-$C_{20}$), derivatives thereof, or combinations thereof. In one or more embodiments, the Fischer-Tropsch products via line 120 and/or line 145 can include one or more oxygenated hydrocarbons, olefinic hydrocarbons, paraffinic hydrocarbons, or combinations thereof. The majority of the hydrocarbons via line 120 and/or line 145 can be normal ("linear") paraffins. The Fischer-Tropsch products can include, but are not limited to, diesel fuels, kerosene, aviation fuels, propane, butane, LPG, lubricants, naphtha, gasoline, detergents, lubricants, refinery/petrochemical feedstocks, other transportation fuels, synthetic crude oil, liquid fuels, alpha olefins, derivatives thereof; mixtures thereof, or combinations thereof.

In one or more embodiments, the reaction zone 110 can include any suitable catalyst in any suitable configuration or form. In one or more embodiments, the catalyst can be a liquid, a solid, or a combination thereof. Fischer-Tropsch catalysts, as well as most other chain-growth catalysts, can be solid, typically metals or metal-containing compounds. In one or more embodiments, as discussed above, the reaction zone 110 can include a single reaction zone or multiple reaction zones separated by intervening distillation zones 115. Catalyst can be supported in fixed beds, in trays, and/or as a slurry.

In one or more embodiments, the reaction zone 110 can include random, dumped catalyst formed from various ceramic support shapes, fixed catalyst beds, or slurry beds. In one or more embodiments, the catalyst can be supported on one or more packing materials. The particular type of catalyst bed can be determined by the requirements for a specific catalyst, availability, cost, desired end products, and other factors readily determined by one skilled in the art of distillation. In one or more embodiments, the reaction can proceed in a gas phase, a liquid phase, supercritical phase, or a combination thereof.

In one or more embodiments, a Fischer-Tropsch reaction catalyst may include, but is not limited to, cobalt, iron, or ruthenium, derivatives thereof, or combinations thereof. In one or more embodiments, the catalyst can be supported on an inorganic oxide support, such as silica, alumina, silica-alumina, or zinc oxide. In one or more embodiments, the catalyst can include a promoter such as potassium, ruthenium, platinum, palladium, aluminum, rhenium, hafnium, cerium, lanthanum, titanium, chromium, zirconium, derivatives thereof, or any combination thereof. In one or more embodiments, determining appropriate reaction zone 110 properties can be based at least in part on the availability of particular components, the desired product, the particular operating conditions, and the like. For example, cobalt catalysts can provide primarily straight-chain alpha-olefins, while catalysts containing copper can provide alcohols.

In one or more embodiments, the number, length, and/or volume of the reaction zone 110 can be optimized for a given reaction, catalyst, reaction kinetics, and the like. A longer reaction zone can promote more complete reaction, but typically requires more catalyst and thus greater expense. Also, it can be more difficult to maintain isothermal or near-isothermal conditions within the reaction zone 110 having a longer length, larger volume, or both.

In one or more embodiments, the reaction zone 110 can be maintained at a temperature ranging from a low of about 100° C., about 140° C., or about 150° C. to a high of about 350° C., about 450° C., or about 550° C. For example, the reaction zone 110 can be operated at a temperature ranging from about 175° C. to about 250° C., from about 185° C. to about 240° C., or from about 190° C. to about 232° C. In one or more embodiments, the reaction zone 110 can be operated at a pressure ranging from a low of about 0.1 MPa, about 0.5 MPa, or about 1 MPa to a high of about 20 MPa, about 25 MPa, or about 30 MPa. For example, the reaction zone 110 can be operated at a pressure ranging from about 0.1 MPa to about 22 MPa, from about 2 MPa to about 15 MPa, from about 1.5 MPa to about 4 MPa, from about 1 MPa to about 2.5 MPa, or from about 0.1 MPa to about 2.5 MPa.

In one or more embodiments, the distillation zone 115 can include one or more distillation media configurations. In one or more embodiments, the distillation zone 115 can be empty, partially filled, or completely filled with one or more trays and/or packing to improve mass transfer and/or separation of a multi-component fluid. Illustrative trays can include, but are not limited to, perforated trays, sieve trays, bubble cap trays, floating valve trays, fixed valve trays, tunnel trays, cartridge trays, dual flow trays, baffle trays, shower deck trays, disc and donut trays, orbit trays, horse shoe trays, cartridge trays, snap-in valve trays, chimney trays, slit trays, or any combination thereof In one or more embodiments, the packing material can include, but is not limited to, one or more types of structured packing and/or random packing disposed within the distillation zone 115. The packing material can increase the effective surface area within the distillation zone 115, which can improve the mass transfer within the distillation column 1115. The packing material can be made of any suitable material, for example metals, non-metals, polymers, ceramics, glasses, or any combination thereof. Illustrative examples of random packing material can include but is not limited to, Raschig rings, Lessing rings, I-rings, saddle rings, Berl saddles, Intalox saddles, Tellerettes, Pall rings, U-rings, or any combination thereof. Illustrative examples of commercially available structured packing can include, but is not limited to Flexipac® and Gempak® structured packing as manufactured by the Koch-Glitsch Corporation, corrugated sheets, crimped sheets, gauzes, grids wire mesh, monolith honeycomb structures, or any combination thereof In one or more embodiments, independent flanged support screens and hold-downs (not shown) can be fabricated to separate the various sections and prevent packing migration into other sections or components of the distillation column 105. In one or more embodiments, the distillation column 105 can be insulated over a portion or all of its length. The insulation can be calcium silicate block insulation, for example, which may be protected by aluminum shielding. The flanges and other piping components can be insulated with removable glass wool blankets with waterproof outer coverings, for example. In one or more embodiments, the distillation column 105 can include one or more heaters or coolers disposed about a portion of the distillation column 105. For example, in one embodiment a steam jacket or cooling water jacket can be disposed about the reaction zone 110 to provide heat to the reaction zone 110 or to remove heat from the reaction zone 110.

In one or more embodiments, the distillation zone 115 can be operated at similar temperatures and pressures as the reaction zone 110. In one or more embodiments, the distillation zone 115 can be operated at a temperature less than the reaction zone 110. In one or more embodiments, the distillation zone 115 can be operated at a temperature greater than the reaction zone 110. In one or more embodiments, the distillation zone 115 can be operated to include a temperature gradient within the distillation zone 115. For example, the end of the distillation zone 115 disposed toward the second end 109 of the distillation column 105 can be at a temperature greater than the end of the distillation zone 115 disposed toward the reaction zone 110. In one or more embodiments, the difference in the temperature from the end of the distillation zone 115 disposed toward the second end 109 of the distillation column 105 and the end of the distillation zone 115 disposed toward the reaction zone 110 can range from a low of about 5° C., about 10° C., or about 15° C. to a high of about 50° C., about 75° C., or about 100° C.

In Fischer-Tropsch reactions, the heat release can be significant, and in conventional processes this requires special equipment for heat removal and careful control of temperatures. In one or more embodiments, the heat released within the reaction zone 110 can be done so in a boiling environment, which can restrict the temperature within the reaction zone 110 to the boiling temperature of the surrounding medium. Therefore, the heat can be expressed as additional vaporization at the boiling temperature rather than an increase of the temperature within the reaction zone 110. Therefore, a significant portion of the vapor required for the separation within the distillation column 105 can be directly supplied by the reaction, thereby reducing the need for supplying external heat to the distillation column 105.

The distillation column 105 can be made of one or more metallic and/or non-metallic materials physically and chemically compatible with the temperature, pressure, and contents of the distillation column 110. Suitable metallic materials can include, but are not limited to ferrous alloys including carbon and stainless steels, and non-ferrous alloys such as aluminum, nickel, Hastelloy, Inconel, incalloy, tantalum, and the like.

In one or more embodiments, the shell or housing 106 of the distillation column 105 can be horizontal, vertical, or at any angle therebetween. In one or more embodiments, the shell or housing 106 of the distillation column 105 can have any length to diameter (L/D) ratio. For clarity and ease of description, the distillation column 105 discussed herein is with reference to a vertical, cylindrical, distillation column 105 having a reaction zone 110 and a distillation zone 115 and an L/D ratio of greater than 1.

The one or more heat exchangers 125, 150 can be or include any system, device, or combination of systems and/or devices suitable for indirectly transferring heat from one medium to another medium. For example, the one or more heat exchangers 125, 150 can be or include one or more shell-and-tube, plate and frame, spiral wound, U-tube, and/or bayonet style heat exchangers. In one or more embodiments, the one or more heat exchangers 120 can include surface enhanced tubes (e.g. fins, static mixers, rifling, heat conductive packing, turbulence causing projections, or any combination thereof), and the like. In one or more embodiments, the one or more heat exchangers 125, 150 can be air-cooled finned tubing type heat exchangers. The air-cooled finned tubing type heat exchanger can include one or more fans and louvers.

Figure 2:
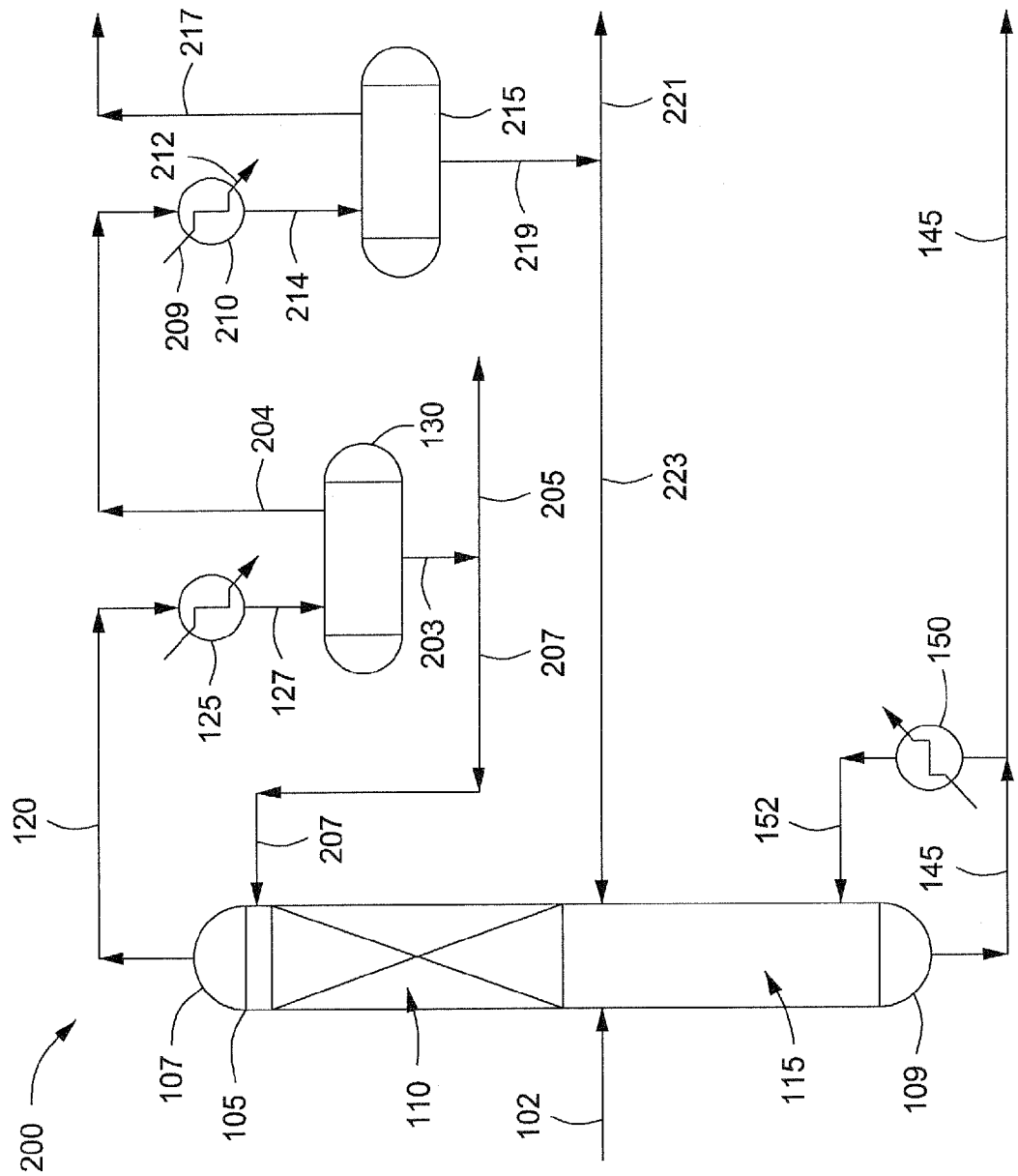
FIG. 2 depicts another illustrative reactive distillation system according to one or more embodiments described.

FIG. 2 depicts another illustrative reactive distillation system 200 according to one or more embodiments. In one or more embodiments, the reactive distillation system 200 can include one or more distillation columns 105, heat exchangers 125, 150, and gas/liquid separation vessels 130. In one or more embodiments, the reactive distillation system 200 can further include one or more heat exchangers 210 and gas/liquid separation vessel 215. The one or more heat exchangers 210 and gas/liquid separation vessel 215 can be similar to the heat exchangers 125, 150 and gas/liquid separation vessel 130 discussed and described above with reference to FIG. 1.

As discussed and described above with reference to FIG. 1, an overhead via line 120 and a bottoms via line 145 can be recovered from the distillation column 105. The overhead via line 120 can be cooled by heat exchanger 125, which can be introduced via line 127 to the gas/liquid separation vessel 130. A liquid product via line 203 and uncondensed gases via line 204 can be recovered from the gas/liquid separation vessel 120 as discussed and described above. In one or more embodiments, at least a portion of the liquid product in line 203 can be recovered as a heavy product via line 205. In one or more embodiments, at least a portion of the heavy product via line 207 can be recycled to the reaction zone 110. In one or more embodiments, at least a portion of the heavy product in line 203 can be recycled via line 207 to the end of the reaction zone 110 disposed toward the first end 107 of the distillation column 105. In one or more embodiments, at least a portion of the heavy product in line 203 can be recycled via line 207 to the end of the reaction zone 110 disposed toward the distillation zone 115.

In one or more embodiments, at least a portion of the uncondensed gases in line 204 can be introduced to the one or more heat exchangers 210. In one or more embodiments, the one or more heat exchangers 210 can indirectly transfer heat from the uncondensed gases introduced via line 204 to a heat transfer medium introduced via line 209. Cooling at least a portion of the uncondensed gases can condense at least a portion of the gases to provide a cooled product via line 214 of which at least a portion includes a condensed or liquid product. A warmed heat transfer medium via line 212 can be recovered from the one or more heat exchangers 210.

The cooled product in line 214 can be introduced to the gas/liquid separation vessel to provide a liquid product via line 219 and uncondensed gases can be recovered via line 217. In one or more embodiments, at least a portion of the condensed product in line 219 can be recovered as a light product via line 221. In one or more embodiments, at least a portion of the light product in line 219 can be recycled to the reaction zone 110 via line 223. In one or more embodiments, at least a portion of the light product in line 219 can be recycled via line 223 to the end of the reaction zone 110 disposed toward the distillation zone 115, to the distillation column 105 between the distillation zone 115 and the reaction zone 110, directly to the reaction zone 110, or any combination thereof. In one or more embodiments, at least a portion of the light product in line 219 can be recycled via line 223 to the end of the reaction zone 110 disposed toward the first end 107 of the distillation column 105.

Although not shown, in at least one specific embodiment the uncondensed gases in line 204 can be recycled to the end of the reaction zone 110 disposed toward the distillation zone 115, to the distillation column 105 between the distillation zone 115 and the reaction zone 110, directly to the reaction zone 110, or any combination thereof.

The heavy product in line 207 can have a different composition than the light product in line 223. In one or more embodiments, the heavy product in line 207 can include heavier or larger molecular sized compounds than the light product in line 223. In other words, the heavy product in line 207 can include hydrocarbons having a higher boiling point than the second portion in line 223.

In one or more embodiments, an example of one particular mode of operation of the reactive distillation system 200 carrying out a Fischer-Tropsch reaction, under steady state operating conditions can be as follows. A reactant containing $H_2$ and CO via line 102 can be introduced to the reaction zone 110. The overhead via line 120 can include primarily $C_1$ to $C_{11}$ hydrocarbons and the bottoms via line 145 can include primarily $C_{12}$ to $C_{16}$ hydrocarbons. The heavy product in line 203, 205, and/or 207 can include $C_8$ to $C_{11}$ hydrocarbons, and the uncondensed gases via line 204 can include $C_1$ to $C_7$ hydrocarbons. The uncondensed gases in line 204 can be cooled in the heat exchanger 215 and separated in the gas/liquid separation vessel 215 to provide a light product via line 219, 221, and/or 223 that includes $C_3$ to $C_7$ and uncondensed gases via line 217 that includes $C_1$ to $C_2$.

Referring to FIGS. 1 and 2, recycling at least a portion of the overhead via line 138, line 140, 207, and/or 223 might seem counter-intuitive because one major advantage of reactive distillation is that the process performs a reaction and a separation in a single apparatus. Recycling at least a portion of the overhead in line 120 via line 138, line 140, line 207, and/or line 223 to the distillation column 105 can counteract the separation efficiency because distillation efficiency is based in part on a temperature gradient. In other words, reducing the temperature gradient within the reaction zone reduces separation efficiency.

Surprisingly, however, it has been discovered that recycling a portion of the overhead, e.g. via line 138, line 140, line 207, and/or line 223, provides control over the distribution of compounds in the reaction zone 110 based on the molecular weight of the compounds while at isothermal or near isothermal conditions. A molecular weight composition gradient refers to the distribution of molecules within the reaction zone 110 based on the molecular weight of the various molecules present within the reaction zone 110. As the hydrocarbon chain length increases, the boiling point of the product also increases. By controlling the temperature in the reaction zone 110, higher boiling products, i.e. those with longer chain lengths can flow from the reaction zone 110 to the distillation zone 115. The tendency for the heavier molecules to flow toward the second end 109 of the distillation column 105 provides a narrower distribution of products in the product slate, because as the compounds reacting within the reaction zone 110 attain the desired size, the compounds flow from the reaction zone 110 and into the distillation zone 115, thereby terminating chain growth of the molecules.

Figure 3:
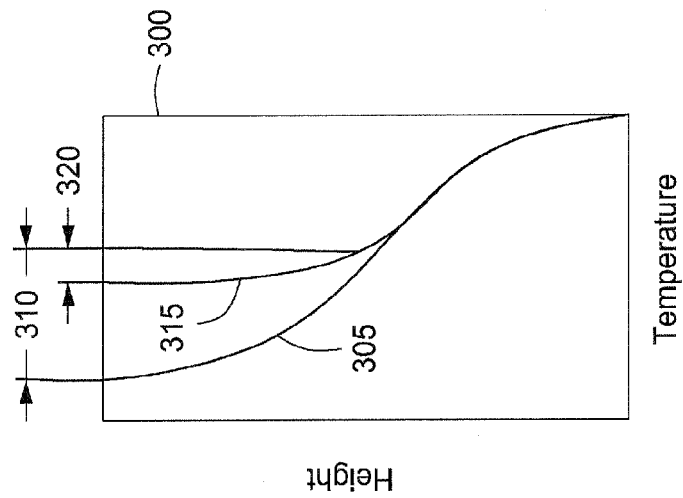
FIG. 3 depicts an illustrative temperature gradient curve of a reactive distillation column according to one or more embodiments described.

FIG. 3 depicts an illustrative temperature gradient curve 300 of a reactive distillation column according to one or more embodiments described. Referring to both FIGS. 1 and 3, line 305 illustrates a representative temperature gradient within the distillation column 105 in the absence of recycling. Line 315 illustrates a representative temperature gradient in the distillation column 105 with the addition of an overhead recycle via lines 138 and 140. As shown, recycling a portion of the overhead reduces the temperature difference within the distillation column 105, yet significantly increases conversion therein.

The reduction in the temperature difference within the distillation column can be substantial. For example, when the distillation column 105 is operated such that the bottom of the reaction zone 110 is at a temperature of about 200° C. to about 235° C., the temperature difference 310 across the reaction zone 110 can be greater than about 20° C., or about 30° C., or about 40° C., or about 50° C., or more. Through recycling, the temperature 320 across the reaction zone 110 can be reduced to about 15° C. or less, about 10° C. or less, about 5° C. or less, or about 2° C. or less. Accordingly, the reaction zone 110 can operate essentially as an isothermal reaction zone. Recycling can reduce the temperature gradient to about 50% of the gradient present in the absence of recycling; or about 30% of the gradient present in the absence of recycling; or about 20% or the gradient present in the absence of recycling; or about 10% of the gradient present in the absence of recycling; or about 5% of the gradient present in the absence of recycling; or about 1% of the gradient present in the absence of recycling.

It should be readily apparent that the disclosed reactive distillation systems 100 and/or 200 discussed above with reference to FIGS. 1 and 2 can be implemented on any conceivable scale from a small skid mounted system to a large fixed installation. For example, the reactive distillation systems 100 and/or 200 can be implemented using significantly smaller-scale and simpler equipment compared to that required for conventional Fischer-Tropsch processes. The narrow product slate provided by the reactive distillation systems 100 and 200 discussed herein significantly reduces the need and associated costs of subsequent processing. Thus, the embodiments provided herein are amenable to inclusion in a low cost, skid-mounted gas-to-liquid processing unit. Furthermore, the elimination of a great deal of the complexity of a conventional unit makes the embodiments provided herein practical for small scale applications that are not considered economical using conventional technology. A skid-mounted configuration can include provisions for raising and lowering the reactive distillation column for ease of transport. A skid-mounted system can be implemented as a structure about thirty feet high and having a footprint that is about sixteen by sixteen feet, for example.

The simplicity of the embodiments provided also makes these embodiments useful for unattended operations in remote locations, such as at or near a well site. Furthermore, the disclosed reactive distillation systems 100 and/or 200 can be well suited for gas-to-liquids conversion embodied in a skid-mounted unit, especially when used in conjunction with a small scale process for providing syngas, such as the system discussed and described in U.S. Pat. No. 7,033,569. Such conversion can also be implemented in remote locations, such as at or near a well site.

EXAMPLES

The foregoing discussion can be further described with reference to the following non-limiting examples. Example 1 represents a reactive distillation according to one or more embodiments described, and illustrates the surprising and unexpected results using a primary and secondary recycle to the reaction zone. Comparative Example 1 shows the results of a reactive distillation with only a primary recycle and not a secondary recycle.

In each example, a Fischer-Tropsch reaction was conducted within a vertical reactive distillation column having a configuration similar to that shown in column 105 of FIG. 1. The column diameter was 3", the reaction bed length was 10 ft, and the distillation zone has a length of 8 ft. The distillation zone of the column was filled with ½" ceramic saddles. The catalyst was 10 to 25 weight percent cobalt on ⅛" alumina spheres. The spheres were packaged in ½" diameter stainless steel mesh tubes to allow sufficient open cross section in the column to prevent flooding.

In each example, 2,2,4 tri-methyl pentane was used as the starting material. Such pure material was chosen because it cannot be produced by a Fischer-Tropsch reaction. The start up material was used to heat the reaction bed to a temperature of about 390° F. to 405° F., before beginning the Fischer-Tropsch reaction within the column.

Comparative Example 1

Figure 4:
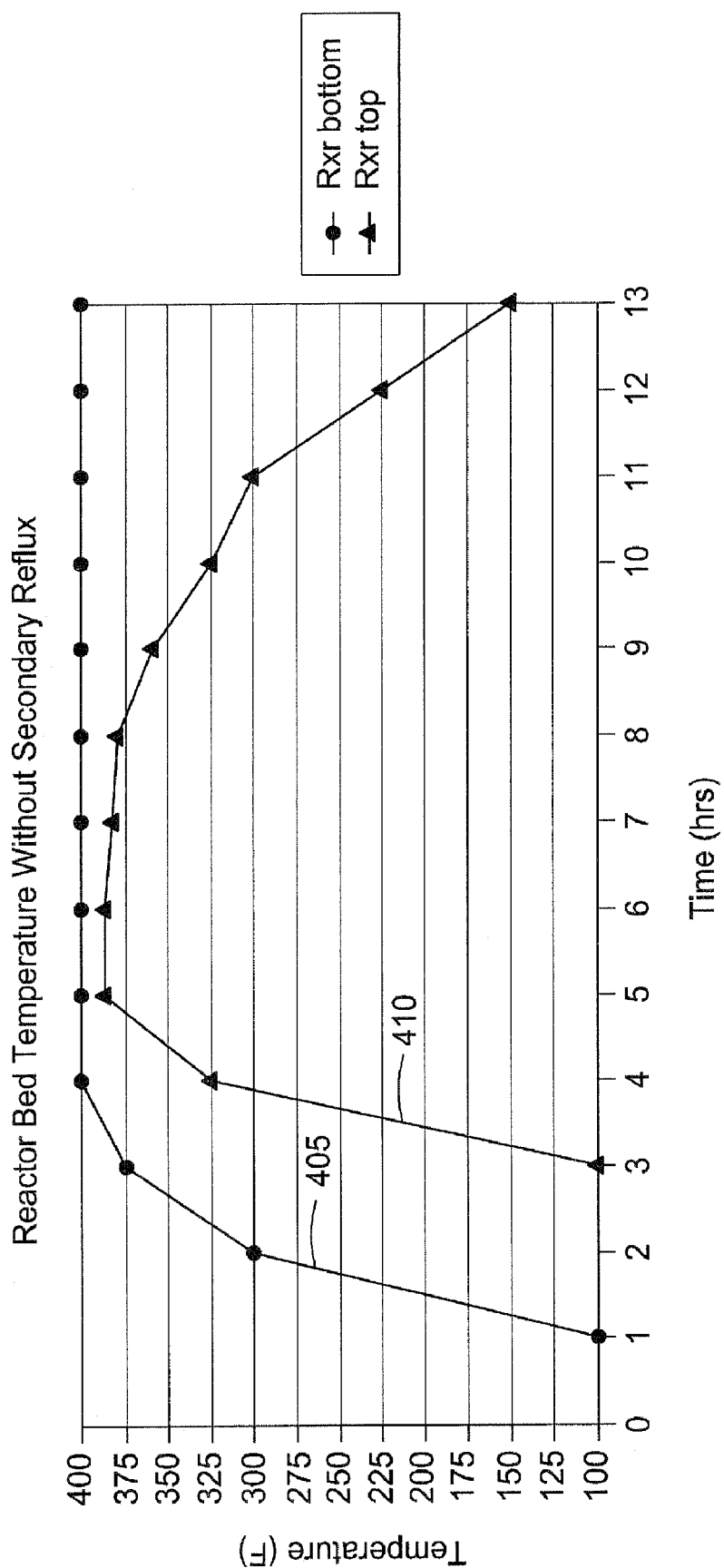
FIG. 4 is a graphical representation of reaction bed temperature versus time for an illustrative reaction bed without a secondary recycle.
Figure 5:
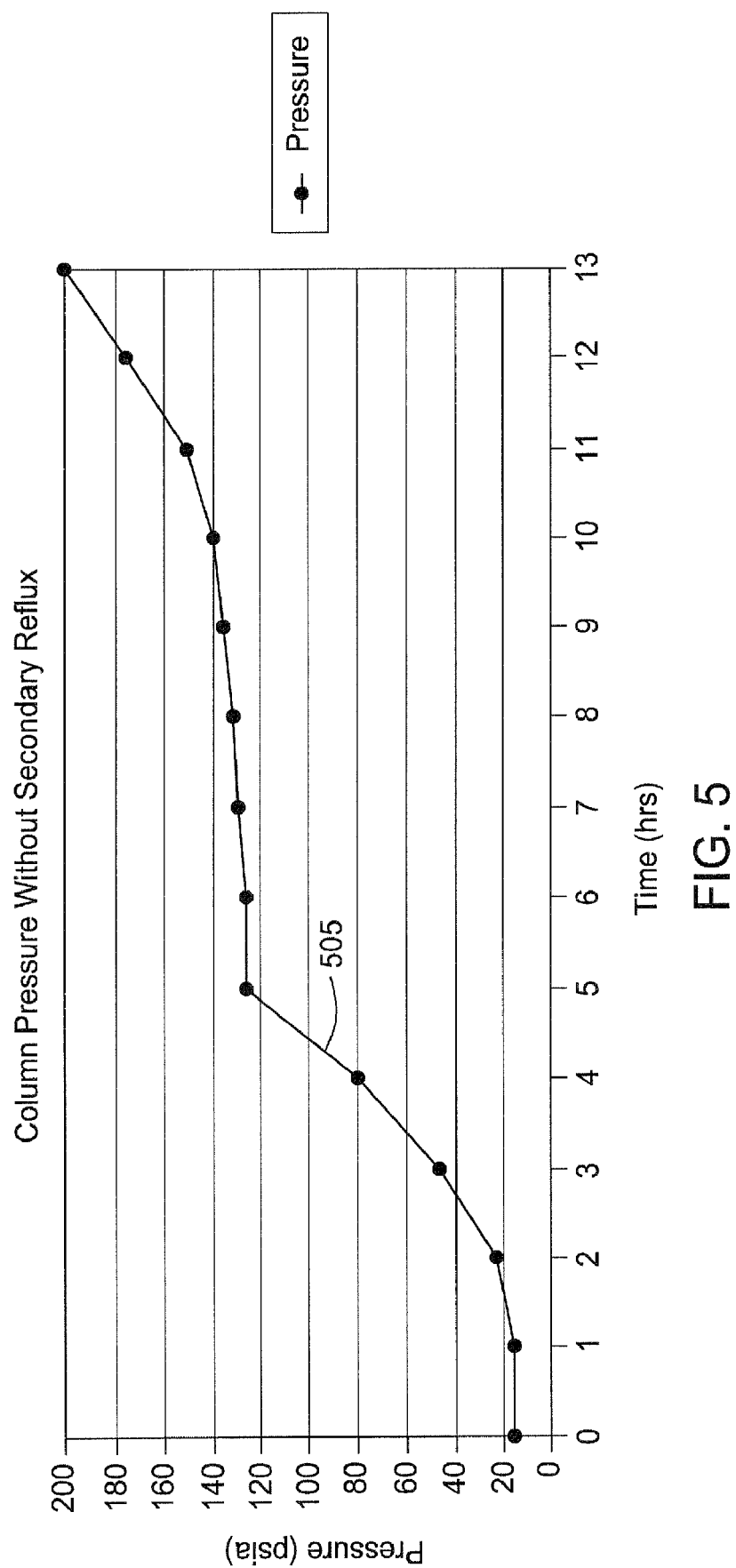
FIG. 5 is a graphical representation of column pressure versus time for an illustrative reaction bed without a secondary recycle.

FIG. 4 is a graphical representation of the reaction bed temperature versus time and FIG. 5 is a graphical representation of the column pressure versus time. After a stable temperature profile within the reaction bed was achieved, i.e. the temperature difference from a first end of the reaction bed (curve 410) to a second end of the reaction bed (curve 405), was about 10° F. or less, the reactants were introduced to the reaction bed, which occurred at about 5 hours. The reactants were a 2:1 mixture of $H_2$ and CO.

A primary recycle was then introduced to the first end of the reaction bed at a rate of 2 liters per minute. After several minutes, the overhead samples contained less than 1 mol % ethylene and propylene. The bottoms samples showed only the pure material that was used as the start-up material.

The temperature at the second end of the reaction bed (curve 405) was maintained at about 400° F. The pressure of the column (curve 505) increased from about 125 psig to more than 200 psig while the temperature at the top of the reaction bed (curve 410) continued to decrease to below 150° F. after 13 hours. As the temperature decreased, the production rate of ethylene and propylene in the overhead also decreased. Specifically, at about 325° F. in the first end of the reaction bed, which occurred at about 10 hours, the production rate of ethylene and propylene in the overhead decreased, which caused the column pressure to increase from about 140 psig to above 200 psig and the temperature to decrease to below 150° F., as the reactants continued to enter the column.

Example 1

The same reactor configuration and catalyst were used as described above in the previous comparative example. This time a secondary recycle was fed to the column.

After a stable temperature profile within the reaction bed was achieved, i.e. the temperature difference from a first end of the reaction bed (curve 610) to a second end of the reaction bed (curve 605), was about 10° F. or less, the reactants were introduced to the reaction bed, which occurred at about 4 hours. The reactants were a 2:1 mixture of $H_2$ and CO.

Figure 6:
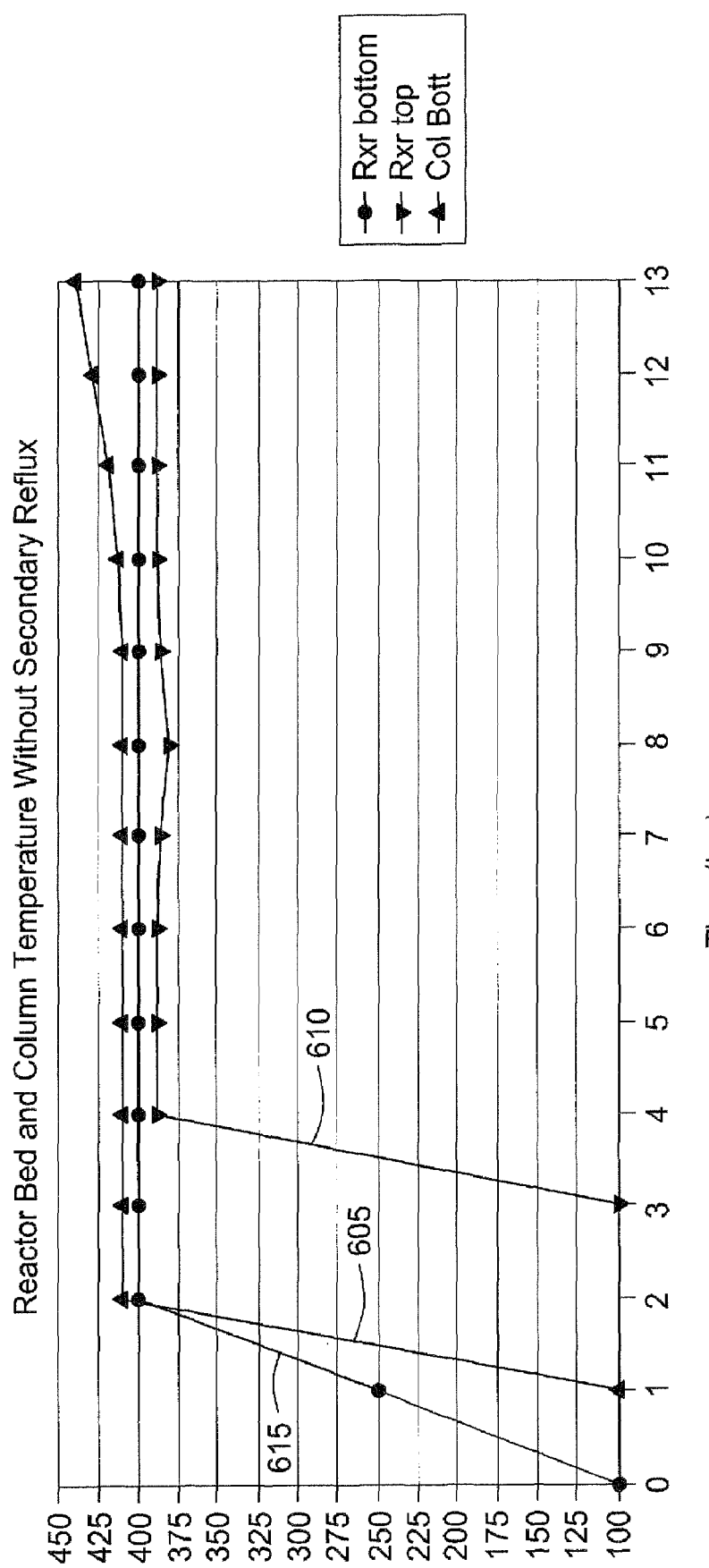
FIG. 6 is a graphical representation of reaction bed temperature versus time for an illustrative reaction bed with a secondary recycle.
Figure 7:
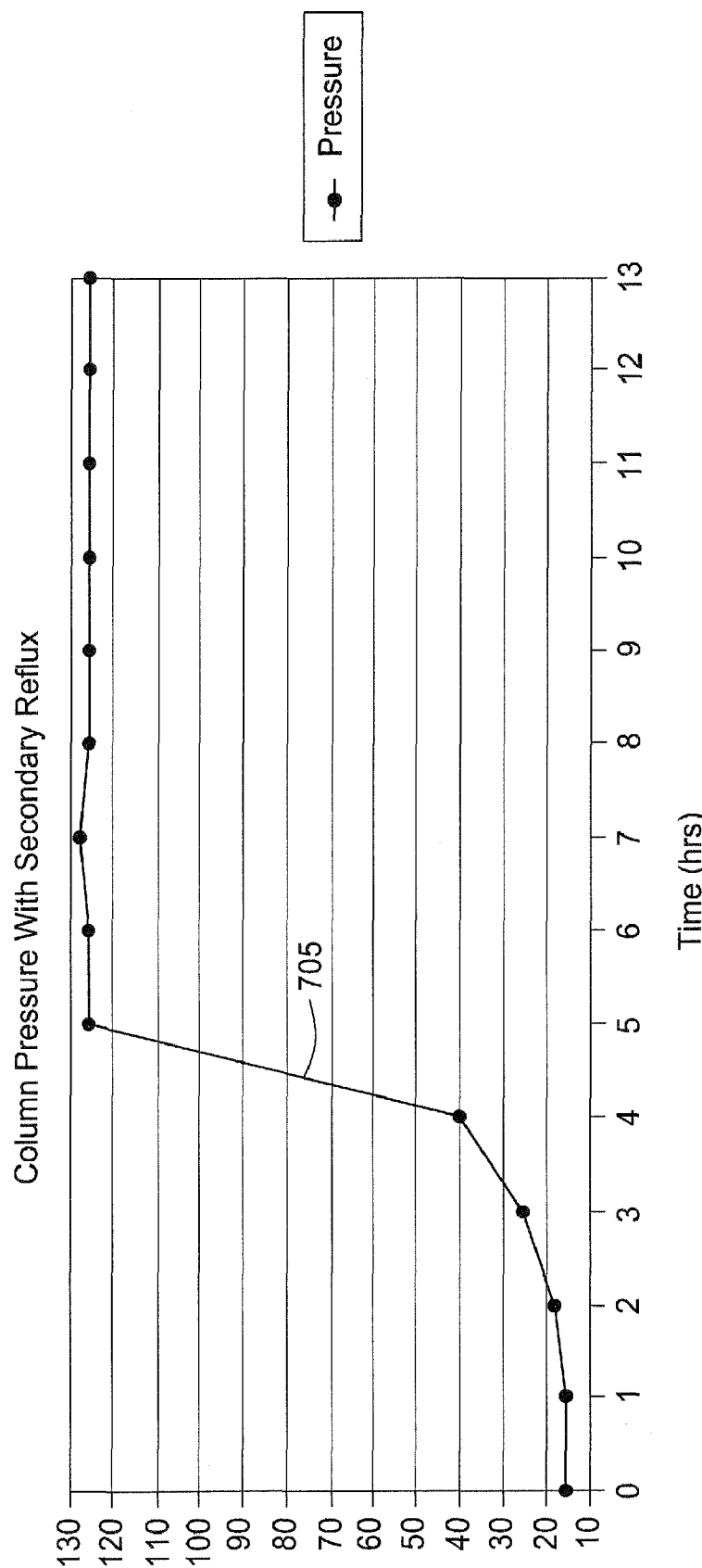
FIG. 7 is a graphical representation of column pressure versus time for an illustrative reaction bed with a secondary recycle.

FIG. 6 is a graphical representation of the reaction bed temperature versus time for the reaction bed with the secondary recycle. FIG. 7 is a graphical representation of column pressure versus time for an illustrative reaction bed with the secondary recycle. As the ethylene and propylene levels in the overhead increased, the temperature at the bottom of the reaction bed remained at 400° F. (curve 605), the temperature at the top of the reaction bed began to decrease (curve 610), and the pressure of the column began to increase (curve 705).

The secondary recycle to the lower portion of the reaction bed was started when the temperature at the top of the reaction bed decreased from about 395° F. to about 385° F. The ethylene and propylene concentration reached a maximum of about one mole percent before starting the secondary recycle. The secondary recycle reversed the temperature decrease at the top of the reaction bed and the associated pressure increase within the column. When a secondary recycle of the overhead was introduced to the lower portion of the reaction bed, the decrease in temperature and increase in pressure was reduced and a stabilized temperature and pressure profile was achieved. The ratio of the primary recycle to the secondary recycle was maintained at about 1:1. The amount of overhead recycled in both the primary recycle and the secondary recycle was about 2 liters per minute.

Still referring to FIGS. 6 and 7, the temperature at the bottom of the reaction bed was maintained at about 400° F. by controlling the reboiler heat input. The temperature at the bottom of the reaction bed dropped to about 390° F. when the secondary recycle was started, but recovered to about 400° F. within about 15 minutes after the secondary recycle was introduced. After the secondary recycle was introduced, the ethylene and propylene concentration in the overhead decreased to about 0.1 mole percent or less and heavier hydrocarbon products began to appear at the bottom of the column. As compounds heavier than the start up material began to accumulate in the bottom of the column, the temperature at the bottom of the column began to increase (curve 615).

Gas chromatography was used to analyze the bottoms recovered from the column. In Example 1, approximately 30 peaks appeared in die column bottoms. The individual species were not identified. Instead a series of known pure compounds were used to divide the gas chromatography ("GC") trace into molecular weight ranges. These molecular weight ranges or "markers" included $C_3$, $C_4$, $C_6$, $C_8$, $C_{10}$, $C_{12}$ and $C_{14}$ hydrocarbons as well as the pure material used as the start-up fluid. This divided the GC trace into a series of ranges and each product peak was assumed to fall in the molecular weight range between the markers. This method was used to generate product range curves for the column bottoms. The curves showed a Gaussian distribution.

The product chain length was a Gaussian distribution about an average chain length. With one theoretical tray the peak distribution of the compounds in the bottoms centered around the $C_7$ hydrocarbon. With 3-4 theoretical trays, the peak distribution of the compounds in the bottoms centered around $C_{11}$-$C_{12}$.

In Comparative Example 1, no product was recovered from the bottom of the column. The increased concentration of the reactants and the light products within the reaction bed that accumulated when the temperature at the top of the reaction bed dropped below 325° F. precluded the Fischer-Tropsch reaction from producing products heavier than the non-reactive startup material.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for producing gas-to-liquids products, comprising:
   reacting a feedstock comprising hydrogen, carbon monoxide, carbon dioxide, or any combination thereof in a column having a distillation zone and a reaction zone to provide a bottoms stream and an overhead stream;
   recycling a first portion of the overhead stream to the column at the top of the reaction zone;
   recycling a second portion of the overhead stream to the column at the bottom of the reaction zone; and
   recovering a third portion of the overhead stream as a product, wherein the product comprises a hydrocarbon, an oxygenated hydrocarbon, or a combination thereof.

2. The method of claim 1, wherein recycling the two portions of the overhead stream reduces a temperature gradient across the reaction zone as compared to a temperature gradient that is present when only the first portion is recycled to the top of the reaction zone.

3. The method of claim 2, wherein the temperature gradient is reduced by more than 50%.

4. The method of claim 3, wherein the column includes a single distillation zone and a single reaction zone disposed therein, and wherein the reaction zone is disposed above the distillation zone such that the bottom of the reaction zone is adjacent a top of the distillation zone.

5. The method of claim 1, wherein the reaction is a hydrocarbon chain growth reaction.

6. The method of claim 1, further comprising separating the overhead stream into a light overhead stream and a heavy overhead stream; recycling the heavy overhead stream to the column at the top of the reaction zone; and recycling the light overhead stream to the column at the bottom of the reaction zone.

7. A method for producing gas-to-liquids products, comprising:
   introducing one or more reactants to a reactive distillation column containing a reaction zone and a distillation zone therein, wherein the one or more reactants comprise hydrogen, carbon monoxide, carbon dioxide, or any combination thereof;
   reacting the one or more reactants in the presence of a catalyst in the reaction zone to provide an overhead and a bottoms product, wherein the overhead and bottoms product comprise a hydrocarbon, an oxygenated hydrocarbon, or a combination thereof;
   separating the overhead into at least a first portion and a second portion; and
   recycling the first and second portions to different locations within the reaction zone, wherein the first portion is recycled to a first end of the reaction zone and the second portion is recycled to a second end of the reaction zone.

8. The method of claim 7, wherein recycling the first and second portions reduces a temperature gradient across the reaction zone by more than 50% as compared to a temperature gradient that is present when only the first portion is recycled to the reaction zone.

9. The method of claim 7, wherein reacting the one or more reactants in the presence of the catalyst comprises a chain growth reaction.

10. The method of claim 7, wherein reacting the one or more reactants in the presence of the catalyst comprises a Fischer-Tropsch reaction.

11. The method of claim 7, wherein the first portion and the second portion comprise the same compounds.

12. The method of claim 7, wherein the first portion comprises compounds having a higher boiling point than the second portion.

13. The method of claim 7, wherein recycling the first portion and the second portion provides a reaction zone temperature gradient from the first end of the reaction zone to the second end of the reaction zone of less than about 20° C.

14. The method of claim 7, wherein the overhead comprises one or more $C_1$ to $C_{10}$ hydrocarbons and the bottoms product comprises one or more $C_4$ to $C_{30}$ hydrocarbons.

15. A method for producing gas-to-liquids products, comprising:
   introducing one or more reactants to a reactive distillation column containing a reaction zone and a distillation zone therein, wherein the one or more reactants comprise hydrogen, carbon monoxide, carbon dioxide, or any combination thereof;
   reacting the one or more reactants in the presence of a catalyst in the reaction zone to provide an overhead and a bottoms product, wherein the overhead comprises a gas, and wherein at least one of the overhead and the bottoms product comprises a hydrocarbon, an oxygenated hydrocarbon, or a combination thereof;
   cooling at least a portion of the overhead to provide a two-phase mixture;
   separating the liquid from the two-phase mixture to provide a first liquid recycle and a first gas recycle;
   recycling at least a portion of the first liquid recycle to the reaction zone; and
   recycling at least a portion of the first gas recycle to the reaction zone, wherein the first liquid recycle and the first gas recycle are introduced to different locations within the reaction zone.

16. The method of claim 15, further comprising:
   cooling at least a portion of the first gas recycle prior to recycling the first gas recycle to provide a second two-phase mixture;
   separating the liquid from the second two-phase mixture to provide a second liquid recycle and a gas product; and
   recycling at least a portion of the second liquid recycle to the reaction zone.

17. The method of claim 15, wherein the first liquid recycle is recycled to a first end of the reaction zone and the first gas recycle is recycle to a second end of the reaction zone, wherein the first liquid recycle is recycled to a top of the reaction zone and the first gas recycle is recycled to a bottom of the reaction zone, wherein recycling the first liquid recycle and the first gas recycle reduces a temperature gradient across the reaction zone by more than 50% as compared to a temperature gradient that is present when only the first liquid recycle is recycled to the top of the reaction zone, and wherein the temperature gradient is less than about 15° C.

* * * * *